(12) United States Patent
Bunt et al.

(10) Patent No.: US 6,776,164 B2
(45) Date of Patent: Aug. 17, 2004

(54) ENHANCED INTRAVAGINAL DEVICES

(75) Inventors: Craig Robert Bunt, Hamilton (NZ); Michael John Rathbone, Hamilton (NZ); Shane Burggraaf, Hamilton (NZ)

(73) Assignee: Interag, Hamilton (NZ)

( * ) Notice: Subject to any disclaimer, the term of this patent is extended or adjusted under 35 U.S.C. 154(b) by 547 days.

(21) Appl. No.: 09/729,251

(22) Filed: Dec. 5, 2000

(65) Prior Publication Data

US 2001/0029357 A1 Oct. 11, 2001

Related U.S. Application Data

(63) Continuation of application No. PCT/NZ99/00070, filed on Jun. 3, 1999.

(30) Foreign Application Priority Data

Jun. 5, 1998 (NZ) .............................................. 330596

(51) Int. Cl.[7] ................................................ A61F 6/06
(52) U.S. Cl. ...................................... 128/830; 128/832
(58) Field of Search .................................. 128/830–841

(56) References Cited

U.S. PATENT DOCUMENTS

| | | | | | |
|---|---|---|---|---|---|
| 3,905,360 A | * | 9/1975 | Zaffaroni | .................... | 128/130 |
| 4,578,076 A | * | 3/1986 | Luukkainen et al. | ........ | 604/892 |
| 4,659,696 A | | 4/1987 | Hirai et al. | .................... | 514/15 |
| 4,732,763 A | | 3/1988 | Beck et al. | ................. | 424/433 |
| 4,883,785 A | | 11/1989 | Chow et al. | ................... | 514/31 |
| 5,116,619 A | | 5/1992 | Greco et al. | ................. | 424/433 |
| 5,690,954 A | * | 11/1997 | Illum | ......................... | 424/434 |
| 5,747,058 A | | 5/1998 | Tipton et al. | ............... | 424/423 |

FOREIGN PATENT DOCUMENTS

| | | |
|---|---|---|
| EP | 0654484 A2 | 5/1995 |
| EP | 0845265 A1 | 6/1998 |
| WO | WO90/03768 | 4/1990 |
| WO | WO91/13634 | 9/1991 |
| WO | WO93/24154 | 12/1993 |
| WO | WO96/14090 | 5/1996 |
| WO | WO97/18245 | 5/1997 |
| WO | WO97/34932 | 9/1997 |
| WO | WO97/40776 | 11/1997 |
| WO | WO98/55148 | 12/1998 |
| WO | WO99/26556 | 6/1999 |

OTHER PUBLICATIONS

Hermens, Pharmaceutisch Weekblad, vol. 14 (4A), "Delivery of Hormones: Somes New Concepts . . . ", pp. 253–257, 1992.

* cited by examiner

*Primary Examiner*—Michael A. Brown
(74) *Attorney, Agent, or Firm*—Jacobson Holman PLLC

(57) ABSTRACT

A biodegradable intra vaginal device for insertion into the vagina of an animal (eg; cattle) useful for herd oestrus synchrony purposes, the device is intra vaginally insertable, intra vaginally retainable and withdrawable by virtue of its ability to change its geometry yet is formed at least almost exclusively from a cyclodextrin and progesterone impregnated moulded matrix of a polyester polymer (eg; poly (ε-caprolactone)) or a starch-like polysaccharide polymer. There is preferably a loading of progesterone of from 0.1 to 3 gms. The surface area of the impregnated matrix is preferably from 15 to 200 cm$^2$.

Related methods and uses also form part of the invention.

28 Claims, 12 Drawing Sheets

ENHANCED INTRAVAGINAL DEVICES

This is a continuation of application No. PCT/NZ99/00070, filed Jun. 3, 1999.

TECHNICAL BACKGROUND

The present invention relates to improvements in and/or relating to intra vaginal devices.

Our PCT/NZ97/00052 (published as WO 97/40776) discloses a variety of different forms of intra vaginal devices of a variable geometry type for retention within the intra vaginal cavity of an animal. Such devices hitherto have primarily involved the use of a silicone rubber composition which as a matrix has been impregnated with an active pharmaceutical agent (eg progesterone). In the variable geometry type devices typified by the CIDR™ devices of this company the impregnated matrix has primarily been supported on a spine of a resilient material such as nylon, the resilience of which is utilised for the variable geometry retention characteristics notwithstanding that such spine is usually fully overlaid with the impregnated matrix.

BACKGROUND ART

Various polymers have been used to deliver pharmaceutical agents, one such class of polymers extensively utilised for the delivery of pharmaceutical agents are the polyesters. Examples of these polymers include poly lactic acid, poly glycolic acid, poly (ε-caprolactone) and various co-polymers of lactide, glycolide and ε-caprolactone.

Pharmaceutical products utilising these polymers are typically formulated as microspheres, microcapsules, films, rods or blocks. Retention within a body cavity has been achieved by a number of methods, eg: the addition of dense fillers, injection or surgical implantation into muscle or subcutaneous areas.

Various agents may be employed to enhance the absorption of agents across mucosal membranes and into the blood circulatory system. One such class of agents extensively utilised for the enhanced absorption of agents are the cyclodextrins. Examples of the cyclodextrins include α-cyclodextrin, β-cyclodextrin, γ-cyclodextrin and hydroxypropyl β-cyclodextrin.

Devices utilising these absorption enhancing agents are typically formulated as microspheres, microcapsules, tablets or liquids.

It is an object of the present invention to provide intra vaginal devices having the prospect of allowing for a given device size or loading an enhanced systemic uptake of an active ingredient or at least provide the public with a useful choice.

DISCLOSURE OF THE INVENTION

The present invention preferably relates to a device designed to deliver progesterone over an extended period of time (2 to 20 days) upon insertion into the vagina of mammals, eg: cattle, sheep, horses, pigs, goats, buffalo or deer. The device is preferably retained within the vagina preferably by means of a flexible geometric arrangement of arms with respect to a body portion.

Accordingly in a first aspect the present invention consists in a device for insertion into the vagina of a mammal, said device consisting of a matrix (preferably mouldable, eg: a polymer) containing both a cyclodextrin and an intra vaginally effective active ingredient.

As used herein, the term "intra vaginally effective active agent" means any compound or composition or complex that by means of delivery into the vaginal cavity of a mammal can be absorbed systemically by the mammal therefrom so as to achieve or suppress some physiological effect. Examples include progesterone (eg: for oestrus synchronisation and other purposes), and oxytocin (eg: for milk let down).

As used herein, the term "cyclodextrin" includes any suitable cyclodextrin or mixtures thereof.

As used herein, the term "polymer" in respect of carrying matrix of the cyclodextrin and intra vaginally effective active agent includes any suitable polymer and need not be restricted to the preferred polymers hereinafter discussed.

In a second aspect the invention consists in an intra vaginal device having at least for a target species of appropriate size a form insertable and retainable in the vaginal tract, said device at least in part having a moulded matrix which includes both a cyclodextrin and an intra vaginally effective active agent.

In still a further aspect the present invention consists in an intra vaginal device for insertion into the vagina of a target species mammal, said device being or having a moulded progesterone and cyclodextrin impregnated matrix of a biodegradable polymer selected from the group of poly esters and starch like polysaccharides, the cyclodextrin being of a kind and in such amount as will enhance release and/or adsorption.

Preferably said kind and amount of cyclodextrin will enhance adsorption.

Preferably said device has a variable geometry whereby after insertion in one geometry the device will assume another having a retention characteristic.

Preferably at least substantially all of the device is said impregnated matrix.

Preferably said polymer is poly (ε-caprolactone).

Alternatively said polymer is a starch-like polysaccharide.

Preferably the cyclodextrin is hydroxypropyl β-cyclodextrin.

Preferably the cyclodextrin comprises from 5 to 70% w/w of the impregnated matrix.

Preferably the progesterone comprises from 5 to 70% w/w of the impregnated matrix.

Preferably the progesterone loading is from 0.1 to 3 gms.

Preferably the surface area of the impregnated matrix is from 15 to 200 $cm^2$.

Preferably progesterone does not appear as a fine powder or crystal upon the surface of the device.

In yet another aspect the present invention consists in an intra vaginal device for insertion into the vagina of an animal, said device being intra vaginally insertable, intra vaginally retainable and withdrawable by virtue of its ability to change its geometry yet being formed at least almost exclusively from a cyclodextrin and progesterone impregnated moulded matrix of poly (ε-caprolactone), the loading of progesterone being from 0.1 to 3 gms and the surface area of the impregnated matrix being from 15 to 200 $cm^2$.

In another aspect the invention is the use, for animal group oestrus synchrony purposes, of a device of the present invention.

In still another aspect the invention is a method of manufacturing of an intra vaginal device as defined which comprises or includes the steps of including in the polymerisable precursor of said biodegradable polymer a distribution of both cyclodextrin and progesterone, and thereafter moulding the device or the impregnated matrix of the device therefrom.

Preferably the whole device results from the moulding.

Preferably the cyclodextrin(s) comprise from from 5 to 70% w/w of the impregnated matrix.

Preferably the progesterone comprises from 5 to 70% w/w of the impregnated matrix.

Preferably said progesterone and cyclodextrin are premixed prior to association with said polymerisable precursor.

In yet a further aspect the invention is a method of achieving in an animal (or in each animal of a group of animals) a blood serum level of progesterone of greater than 2 ng/ml for a period of at least 5 days, said method comprising inserting and retaining in the or each animal for at least the 5 day period a device of the present invention.

Preferably said device has a loading of from 0.1 to 3 gms of progesterone.

Preferably the animal(s) is or are of the cattle, sheep, goats or deer species.

Preferably said device has an impregnated matrix surface of from 15 to 200 cm$^2$.

The invention is also an intra vaginal device of the present invention made by a method of the present invention.

In another aspect the invention is an intra vaginal device substantially as herein described with reference to any one or more of the accompanying drawings.

Preferably all polymer(s) of the said mass (if all, as is preferred, is to be moulded) can be moulded without use of conditions prejudicial to progesterone and any cyclodextrin (or for that matter, any other absorption enhancing agent) present.

The addition of particulate material such as progesterone to silicone in amounts greater than 20% $^w/_w$ has been found to be detrimental to the structural integrity of the intra vaginal inserts. Silicone based intra vaginal inserts must include a spine of a material such as Nylon or stainless steel, over which the silicone is moulded, to maintain a configuration conducive to vaginal retention. The addition of large amounts of particulate material has been found to reduce the strength of the silicone such that the spine may rupture and protrude through the other silicone laminate.

The invention also consists in a method of achieving with an animal (or group of animals) a blood serum level of greater than 2 $^{ng}/_{ml}$ for a period of at least 5 days of progesterone, said method comprising inserting and retaining in the vagina of each animal for at least the 5 day period a device of any of the kinds of the present invention.

Preferably said device has a loading of from 0.1 to 4 gms of progesterone for the target animals such as cattle, sheep, goats, deer, etc.

Preferably said device has an impregnated matrix surface of from 15 to 200 cm$^2$.

The present invention also consists in a method of manufacture of an intra vaginal device which results in a device in accordance with the present invention, and/or vice versa.

DETAILED DESCRIPTION OF THE INVENTION

Preferred forms of the present invention will now be described with reference to FIGS. 1 to 13 in which.

The present invention relates to the discovery that polymers typified by poly (ε-caprolactone) or a starch like saccharide can be appropriately impregnated with an intra vaginally effective active agent such as progesterone (eg: in concentration of from 5% to 70% w/w) and an absorption enhancing agent such as hydroxypropyl β-cyclodextrin (eg: in concentrations of from 5% to 70% w/w) so as to provide appropriate release characteristics for the active agent over the period of intra vaginal retention.

Whilst conventional silicone type polymers may be used they are not normally considered biodegradable in a pasture environment as is, eg; poly (ε-caprolactone). Nevertheless, for the reasons mentioned previously, (ie; including the structural integrity of the silicone where high levels of particulate material are included) other polymers including poly (ε-caprolactone) and starch-like polysaccharides are preferred.

Figure 1:
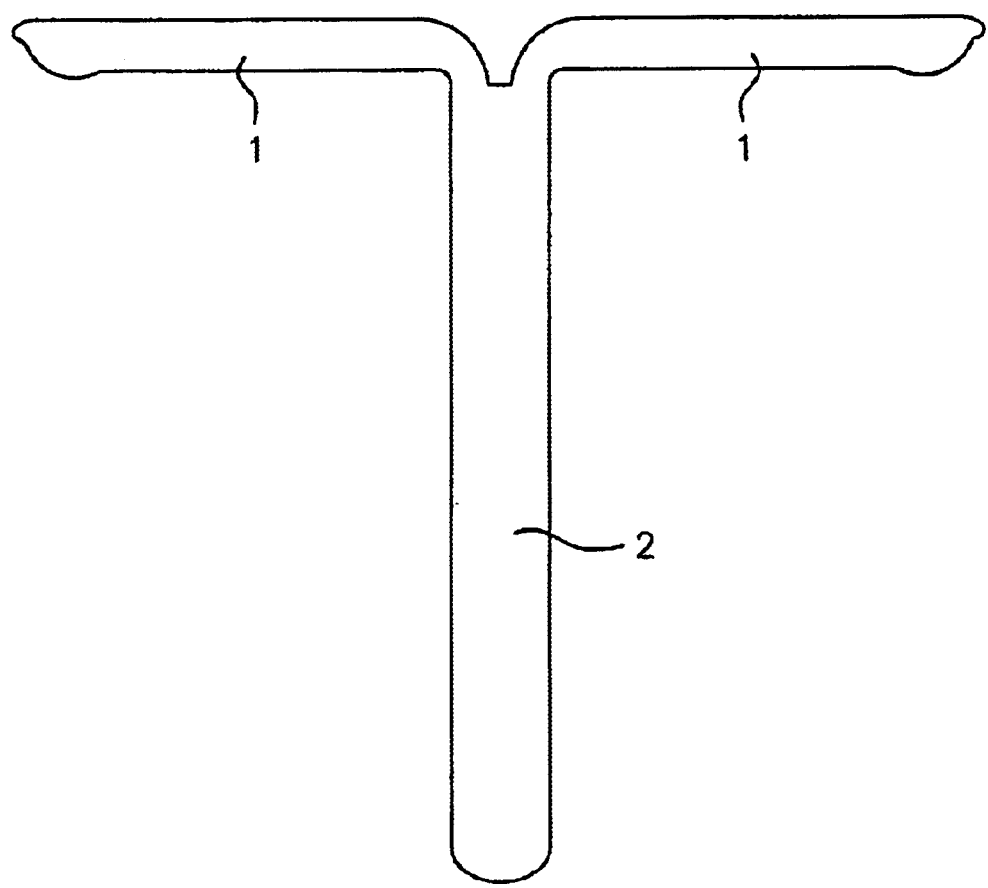
FIG. 1 shows a device of variable geometry (the geometry being variable much in the way as discussed in WO 97/40776) but without a need for a spine of a dissimilar material although if desired that can optionally be present.

In the device of FIG. 1 the preferred device is wholly of the impregnated matrix which is poly (ε-caprolactone) impregnated with hydroxypropyl β-cyclodextrin in the concentration of 5 to 70% w/w.

In FIG. 1 the wings 1 are resilient with respect to the body 2 and in an injection mode can be reduced to a form or assume a position in an applicator in a known manner which facilitates insertion after which the resilience deploys the wings 1 to such condition as is required for retention. The resilience can be subsequently utilised to withdraw the device from within the vagina.

A suitable source of poly (ε-caprolactone) is that product TONE P-767™ available from Union Carbide Specialty Polymers and Products, Danbury, Conn., USA.

Starch-like polysaccharides that can likewise be impregnated and can be used for some or all of the device include MATER-Bi™ available from Novamont, Italy.

A suitable source of hydroxypropyl β-cyclodextrin is that product BETA W7 HP available from Wacker Chemicals Australia, Victoria, Australia.

A preferred method of manufacture of the device is as follows: Polymer (poly (ε-caprolactone), starch-like polysaccharide or a blend of the two) are mixed with active and absorption agent into a mixing vat. The polymer/active/absorption agent mixture is then loaded into the hopper of an injection moulding machine; and processed as a conventional thermoplastic, with machine set point parameters as per technical recommendations of the polymers suppliers literature, and as per injection moulding standard practice.

Key processing points are: barrel temperatures ranging from 60–250° C. with an injection pressure of 1600 bar. Total cycle time due and allowed to cool to equilibrium prior to packaging.

Figure 2:
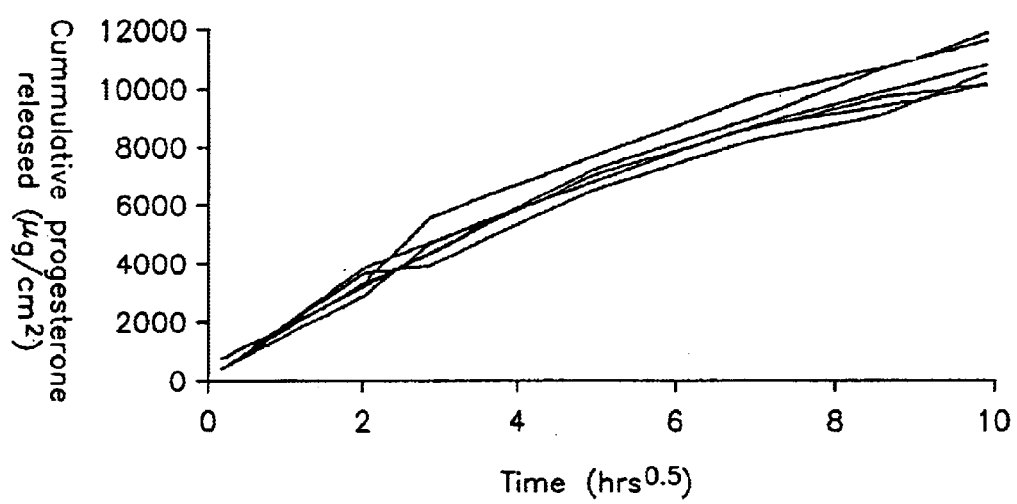
FIG. 2 shows in vitro progesterone release.

FIG. 2 shows an in vitro cumulative progesterone release against the square-root-of-time (inserts manufactured from poly (ε-caprolactone) (thin line) or silicone (thick line)).

Figure 3:
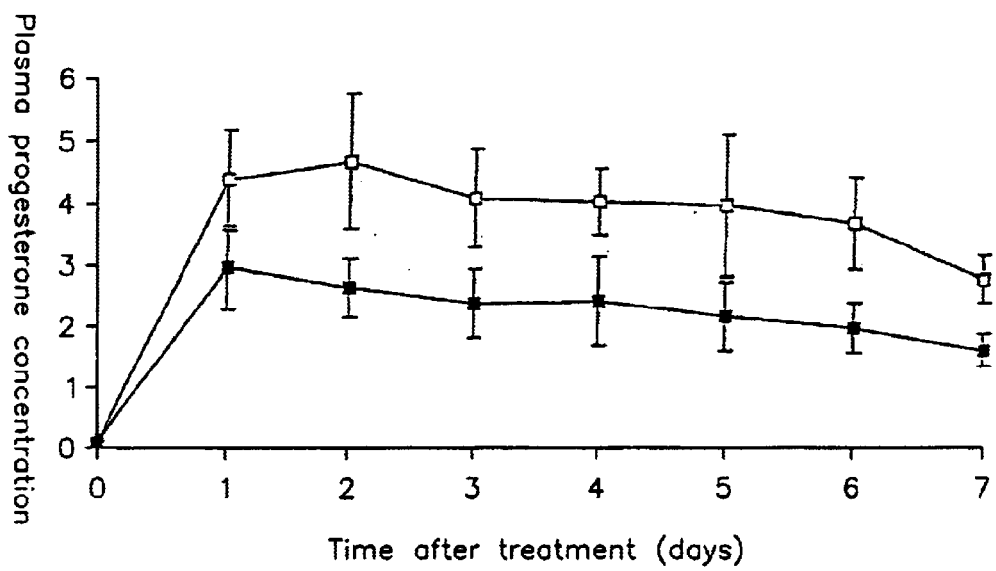
FIG. 3 shows plasma progesterone concentration against time.
Figure 4:
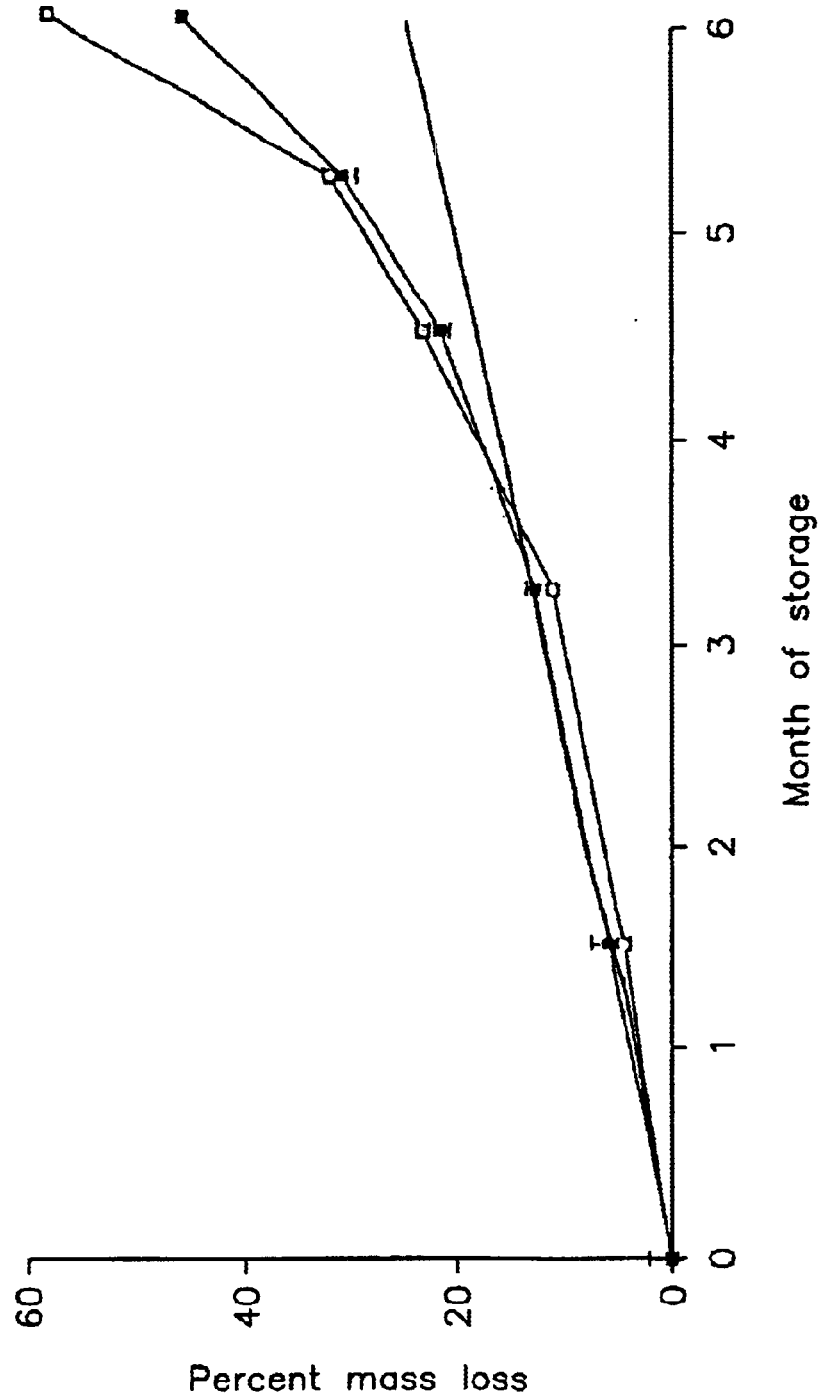
FIG. 4 shows mass lost.
Figure 5:
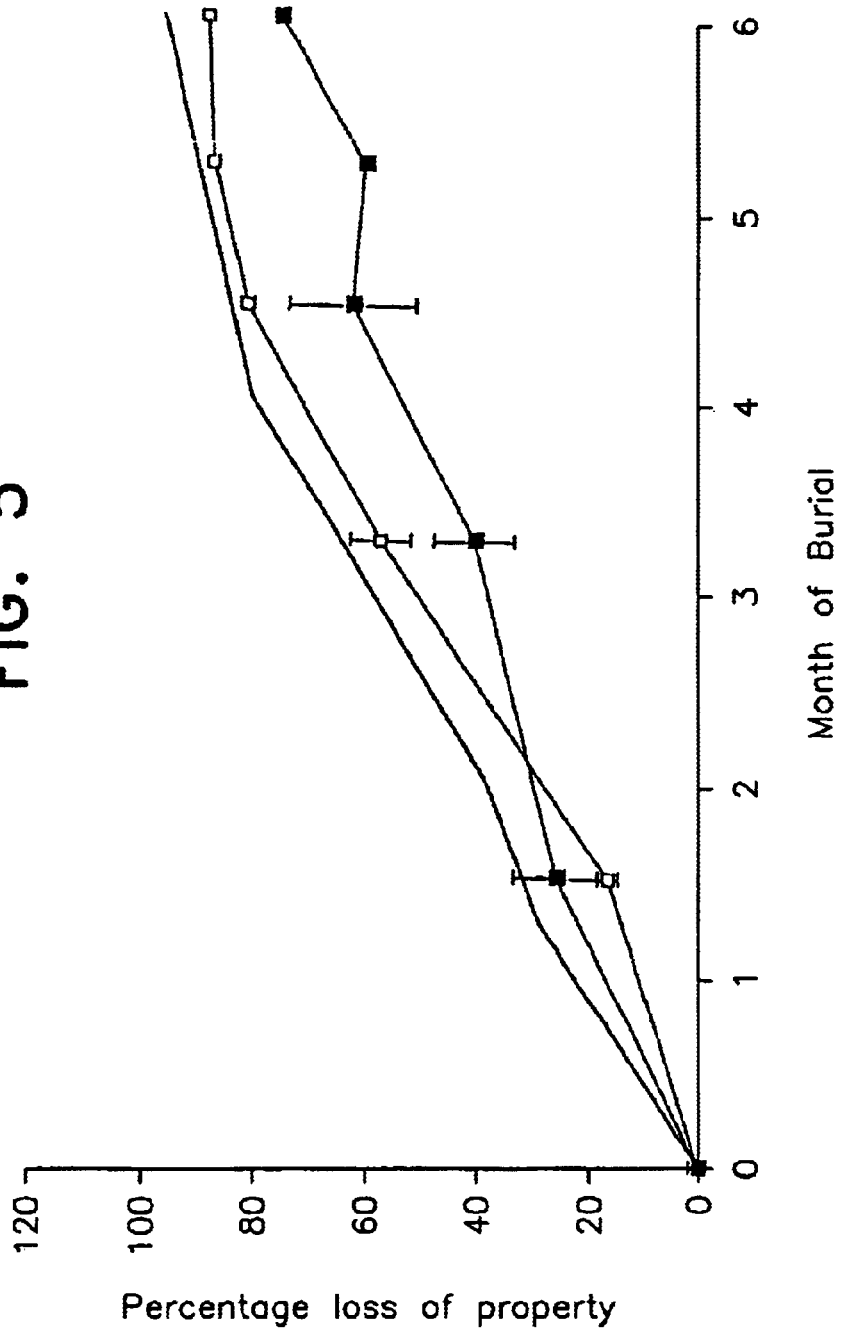
FIG. 5 shows tensile performance.
Figure 6:
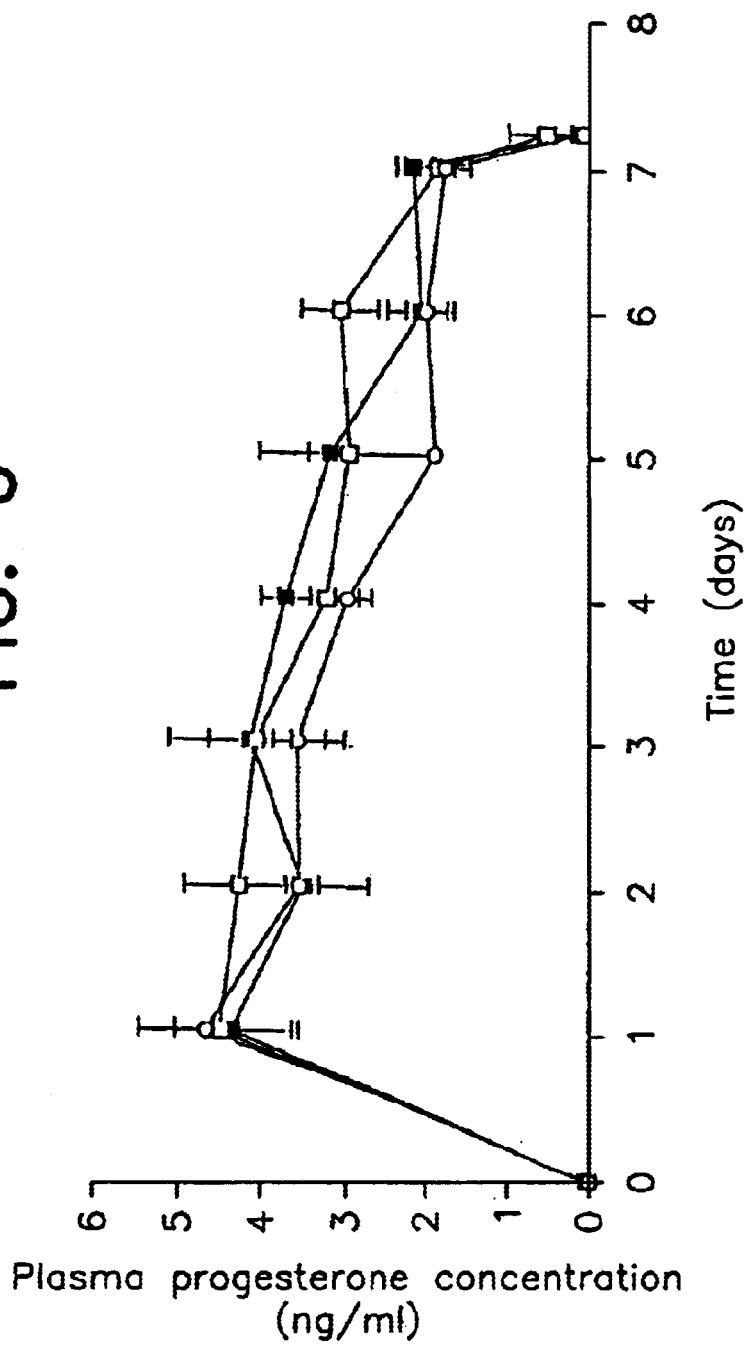
FIG. 6 shows for silicone plasma progesterone concentration against time.
Figure 7:
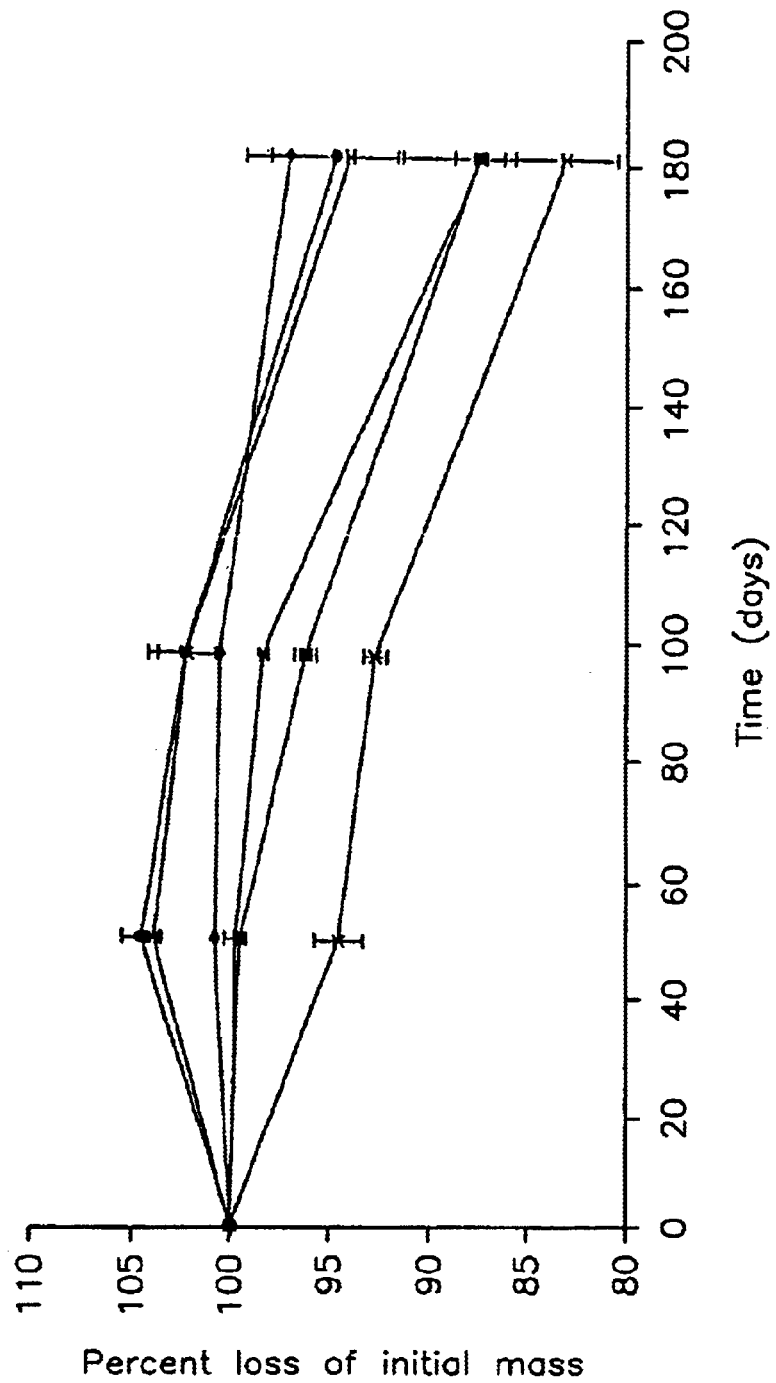
FIG. 7 shows mass loss for poly (ε-caprolactone) formulations.
Figure 8:
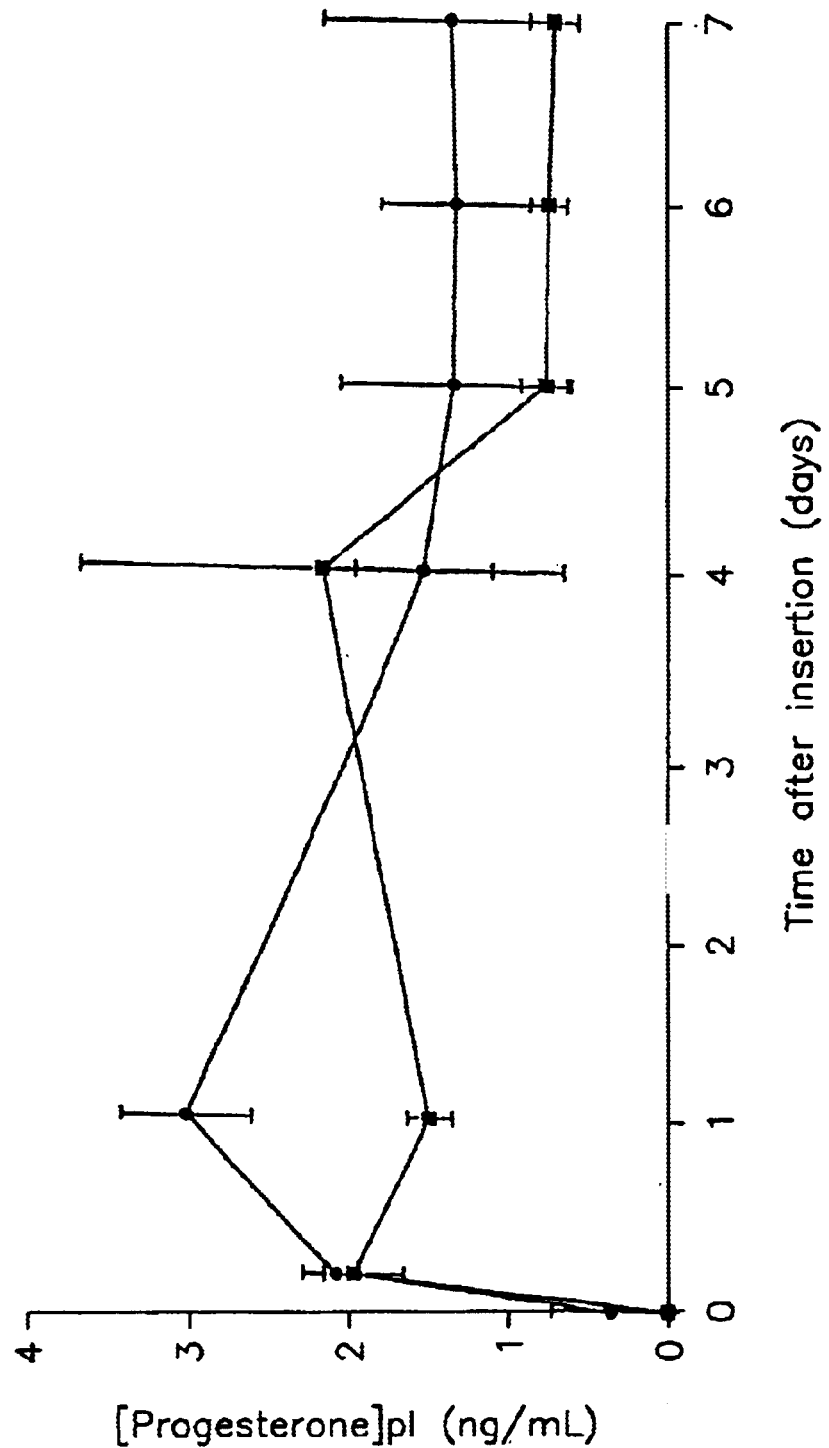
FIG. 8 shows plasma progesterone concentration against time.
Figure 9:
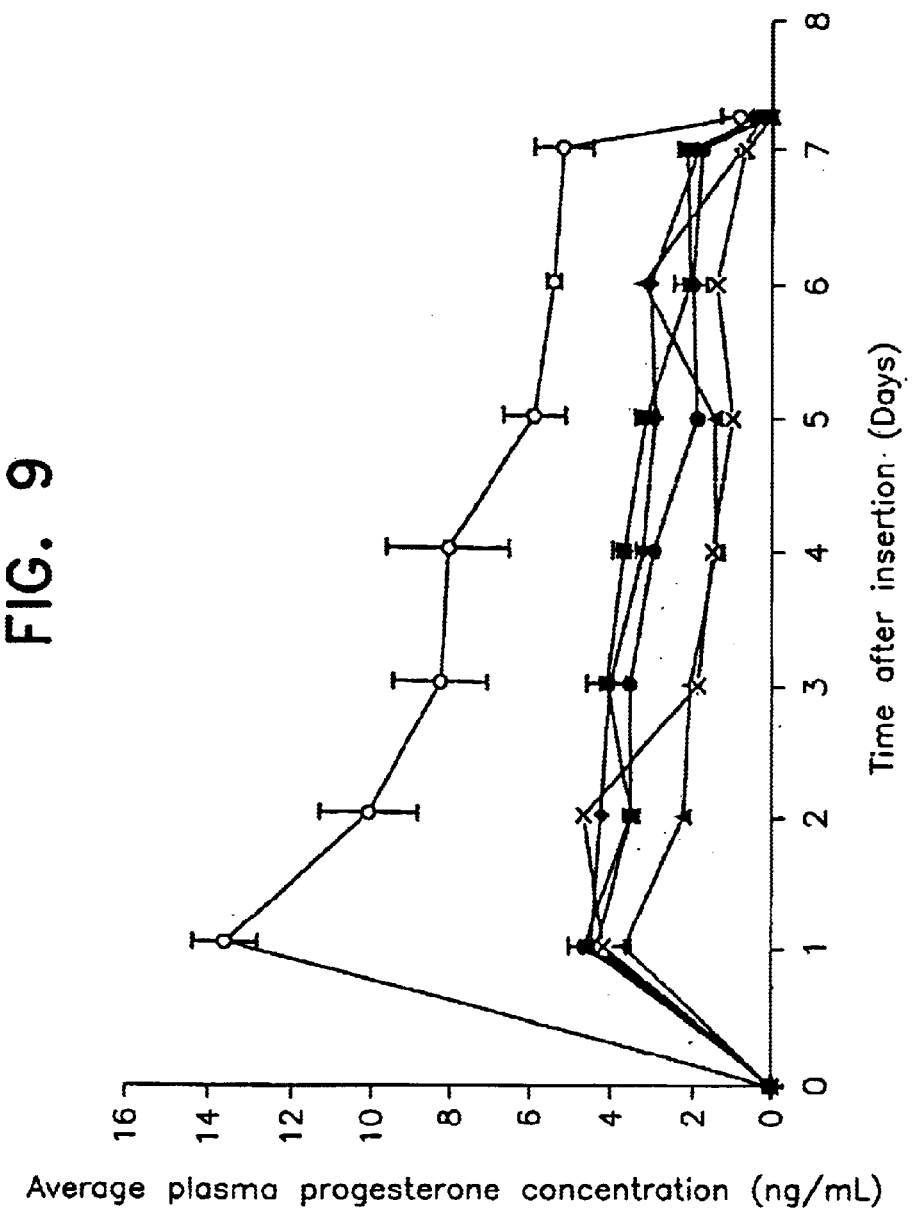
FIG. 9 shows plasma progesterone concentration against time.
Figure 10:
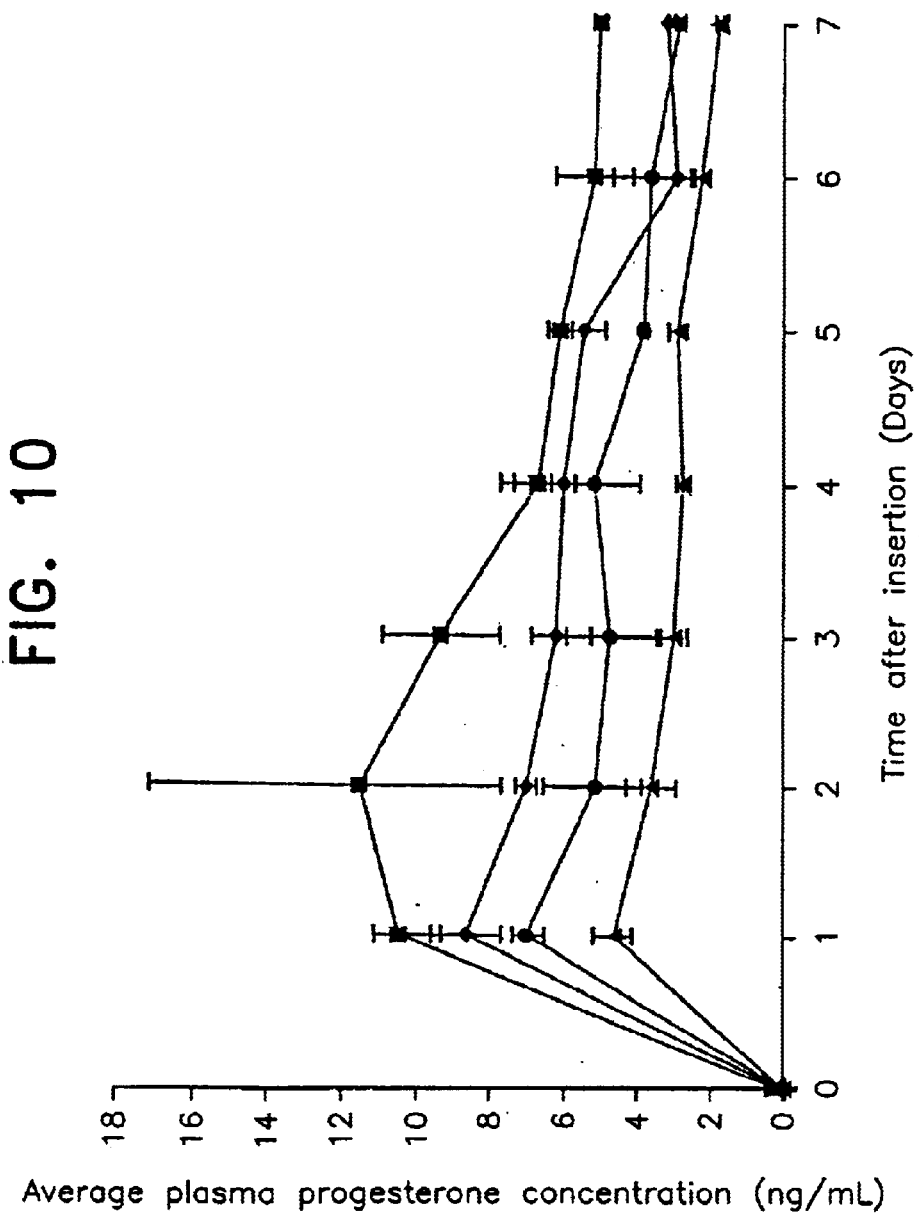
FIG. 10 shows plasma progesterone concentration against time.
Figure 11:
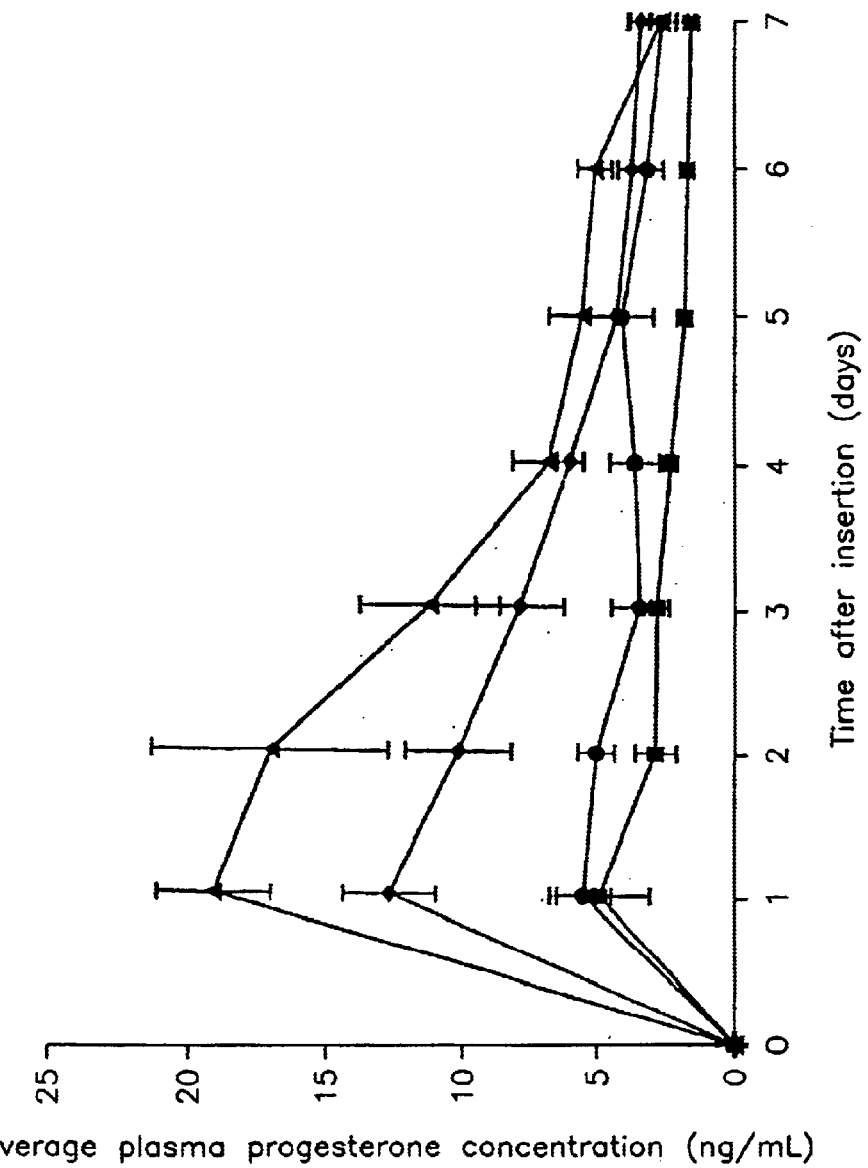
FIG. 11 shows plasma progesterone concentration against time.
Figure 12:
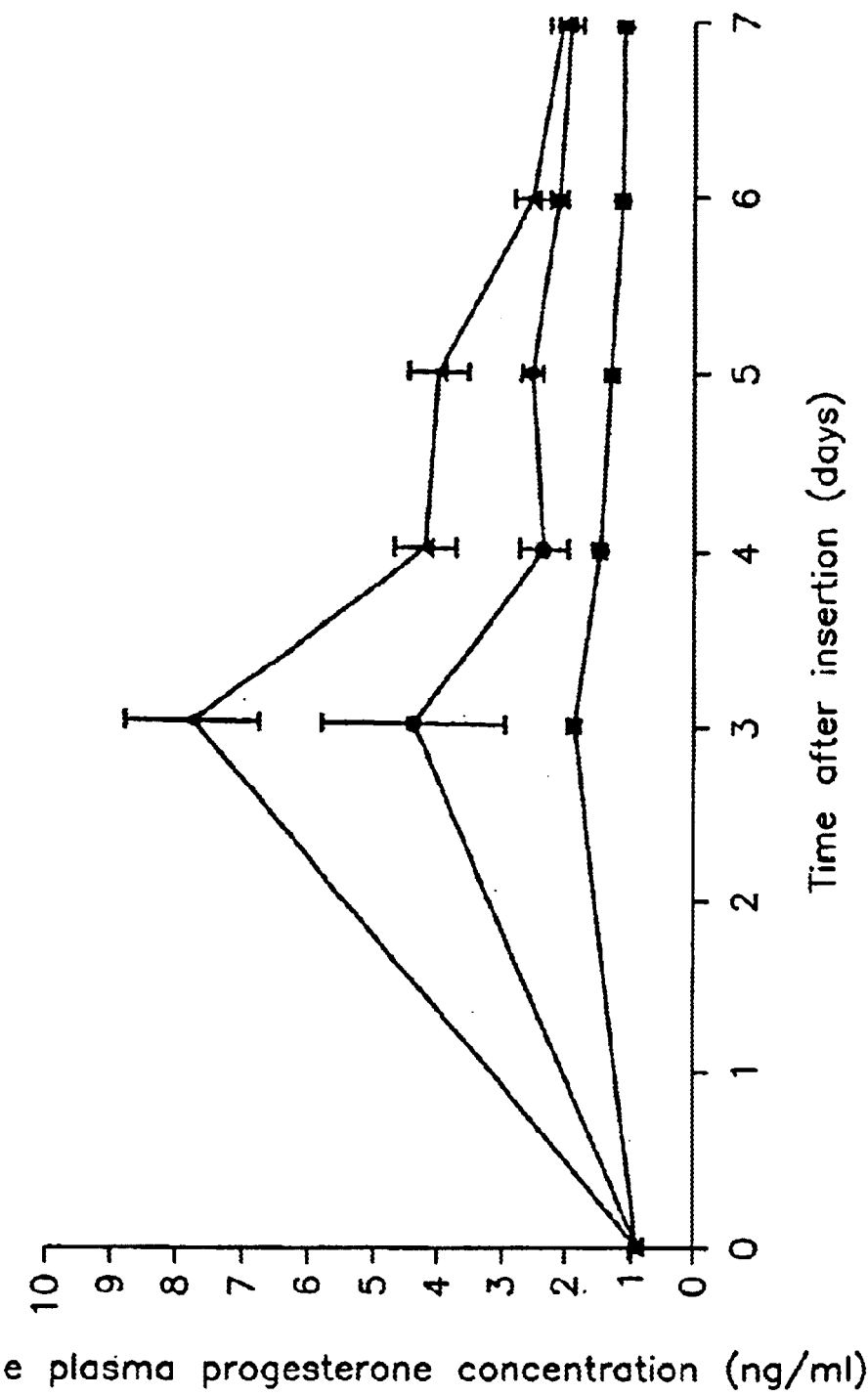
FIG. 12 shows plasma progesterone concentration against time.
Figure 13:
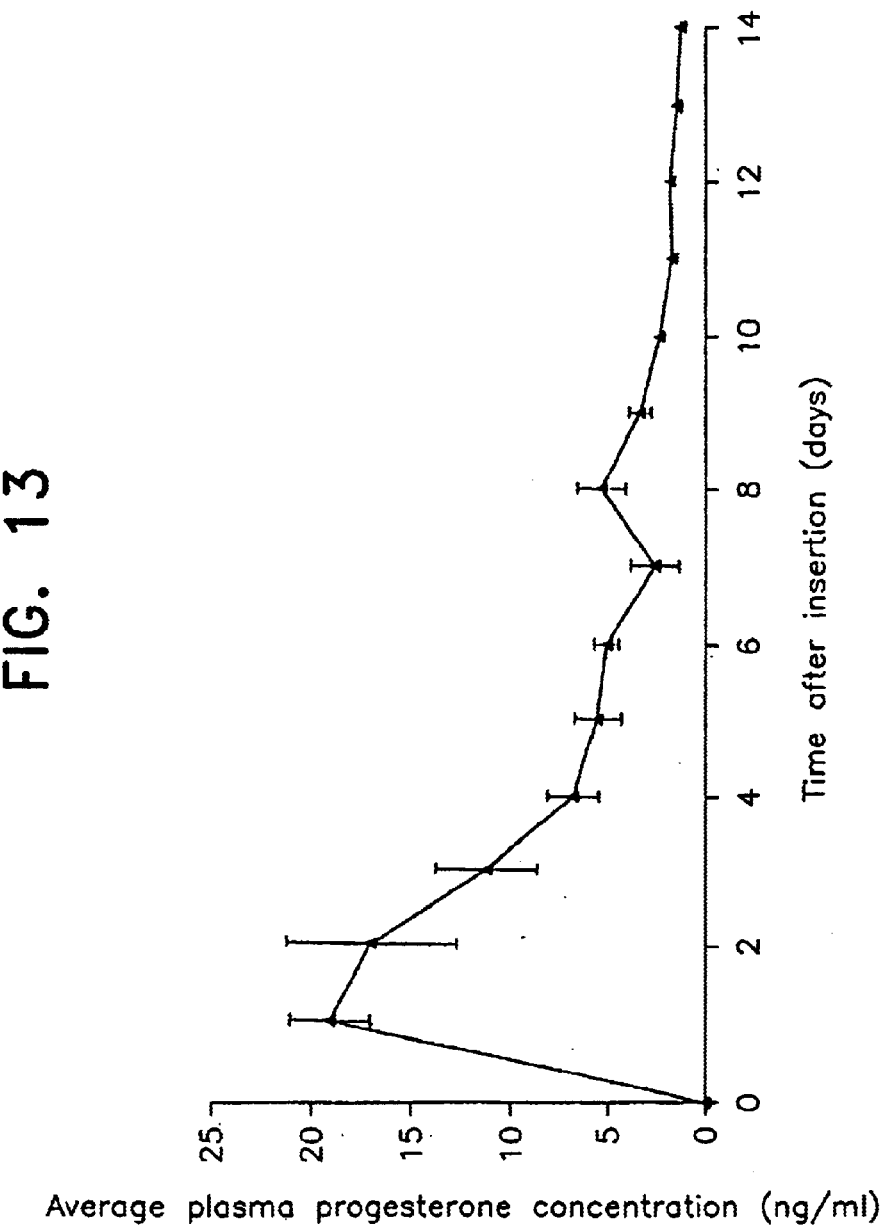
FIG. 13 shows plasma progesterone concentration against time.

FIG. 3 shows an average plasma progesterone concentration against time following two rounds of vaginal treatment with a silicone insert of 134 cm² surface area (□) or a poly (ε-caprolactone) insert of 105 cm² surface area (■), both of which contain 10% $^w/_w$ progesterone (error bars are standard error means (n–12 for silicone inserts, n=9 for poly (ε-caprolactone) inserts)), FIG. 4 shows a percentage of initial mass lost for drug-loaded (■) and blank (□) poly (ε-caprolactone) inserts stored in compost over time (the solid line is the suggested mass loss as per promotional literature supplied by the poly (ε-caprolactone) manufacturer (error bars are ranges (n=2)), FIG. 5 shows a percentage of tensile performance lost for drug-loaded (■) and blank (□) poly (ε-caprolactone) inserts buried in compost over time (the solid line is the suggested tensile performance loss as per promotional literature supplied by the manufacturer. (Error bars are ranges (n=2)), FIG. 6 shows plasma progesterone concentration against time following vaginal treatment for 7 days with a silicone insert of 134 cm² surface area (■), poly (ε-caprolactone) insert of 115 cm² surface area (□) or poly (ε-caprolactone) with lactose insert of 115 cm² surface area (○) (A final plasma sample was collected 6 hours after removal on day 7. (Error bars are standard error means (n–3)), FIG. 7 shows the percentage of initial mass lost for various poly (ε-caprolactone) formulations stored in compost over time [Poly (ε-caprolactone) (♦), poly (ε-caprolactone) with 10% $^w/_w$ progesterone (■), poly (ε-caprolactone) with 12.1% $^w/_w$ lactose and 10.47% $^w/_w$ progesterone (▲), poly (ε-caprolactone) with 37.2% $^w/_w$ β-cyclodextrin and 10.3% $^w/_w$ progesterone (x), poly (ε-caprolactone) with 43.8% $^w/_w$ hydroxypropyl β-cyclodextrin and 10% $^w/_w$ progesterone (*) or poly (ε-caprolactone) with 39.9% $^w/_w$ γ-cyclodextrin and 9.7% $^w/_w$ progesterone (●). (Error bars are ranges (n=2))], FIG. 8 shows plasma progesterone concentration against time following vaginal treatment for 7 days with a Mater-Bi insert of 58 cm² surface area with (■) or without (●) the addition of 20% w/w NaCl. (Error bars are ranges (n=2)), FIG. 9 shows plasma progesterone concentration against time following vaginal treatment for 7 days with various inserts; CIDR cattle insert (■), poly (ε-caprolactone) with 10%$^w/_w$ progesterone (♦), poly (ε-caprolactone) with 12.1%$^w/_w$ lactose and 10.47%$^w/_w$ progesterone (●), poly (ε-caprolactone) with 37.2%$^w/_w$ β-cyclodextrin and 10.3%$^w/_w$ progesterone (▲), poly (ε-caprolactone) with 43.8%$^w/_w$ hydroxypropyl β-cyclodextrin and 10%$^w/_w$ progesterone (○) or poly (ε-caprolactone) with 39.9%$^w/_w$ γ-cyclodextrin and 9.7%$^w/_w$ progesterone (x), FIG. 10 shows plasma progesterone concentration against time following vaginal treatment for 7 days with various inserts; poly (ε-caprolactone) with 44%$^w/_w$ hydroxypropyl β-cyclodextrin and 10%$^w/_w$ progesterone (■), poly (ε-caprolactone) with 22%$^w/_w$ hydroxypropyl β-cyclodextrin and 10%$^w/_w$ progesterone (▲), poly (ε-caprolactone) with 22%$^w/_w$ hydroxypropyl β-cyclodextrin and 10%$^w/_w$ progesterone and 22%$^w/_w$ lactose (♦), poly (ε-caprolactone) with 11%$^w/_w$ hydroxypropyl β-cyclodextrin and 10%$^w/_w$ progesterone and 33%$^w/_w$ lactose (●), FIG. 11 shows plasma progesterone concentration against time following vaginal treatment for 7 days with various inserts; poly (ε-caprolactone) with 5%$^w/_w$ hydroxypropyl β-cyclodextrin and 5%$^w/_w$ progesterone and 30%$^w/_w$ lactose (■), poly (ε-caprolactone) with 20%$^w/_w$ hydroxypropyl β-cyclodextrin and 10%$^w/_w$ progesterone and 30%$^w/_w$ lactose (▲), poly (ε-caprolactone) with 10%$^w/_w$ hydroxypropyl β-cyclodextrin and 10%$^w/_w$ progesterone and 40%$^w/_w$ lactose (♦), poly (ε-caprolactone) with 10%$^w/_w$ hydroxypropyl β-cyclodextrin and 5%$^w/_w$ progesterone and 35%$^w/_w$ lactose (●), FIG. 12 shows plasma progesterone concentration against time following vaginal treatment for 7 days with various inserts; CIDR cattle insert (●), poly (ε-caprolactone) with 10%$^w/_w$ hydroxypropyl β-cyclodextrin and 10%$^w/_w$ progesterone and 50%$^w/_w$ poly ethylene oxide (▲), Mater-Bi with 40%$^w/_w$ γ-cyclodextrin and 10%$^w/_w$ progesterone (■), and FIG. 13 shows plasma progesterone concentration against time following vaginal treatment for 15 days with a poly (ε-caprolactone) with 20%$^w/_w$ hydroxypropyl β-cyclodextrin and 10%$^w/_w$ progesterone and 30%$^w/_w$ lactose (▲).

The choice of a resilient mouldable or shapable "polymer" which is biodegradable is such that degradation of the impregnated matrix (but with a low residual active ingredient loading) will occur over time after removal from the animal after having served its purpose during an intra vaginal insertion of preferably from 2 to 20 days (eg; about 7 days). Minimal degradation (if any) occurs during the period of insertion.

In the device of FIG. 1 the device is wholly of the impregnated matrix which is poly (ε-caprolactone) impregnated with progesterone in the concentration of 5 to 70% w/w without any solid active pharmaceutical agent appearing as a fine powder or crystals on the surface of the device.

Preferably the performance of the device while inserted and its effect upon withdrawal is substantially as discussed in WO 97/40776 but with the advantages of (i) biodegradability after removal from the animal and (ii) the preferred omission of a spine of resilient material.

The preferred biodegradable polymers (typified by poly (ε-caprolactone) or a starch like saccharide) can be appropriately impregnated with an intra vaginally effective active agent such as progesterone (eg: in concentration of from 5% to 70% w/w) and an absorption enhancing agent such as hydroxypropyl β-cyclodextrin (eg: in concentrations of from 5% to 70% w/w) so as to provide appropriate release characteristics for the active agent over the period of intra vaginal retention.

The preferred device is wholly of the impregnated matrix which is poly (ε-caprolactone) impregnated with hydroxypropyl β-cyclodextrin in the concentration of 5 to 70% w/w.

What is claimed is:

1. An intravaginal device being intravaginally insertable, retainable and withdrawable thereafter by virtue of its ability to change its geometry yet being formed solely as a molded progesterone and cyclodextrin impregnated biodegradable matrix of a biodegradable polymer selected from polyesters and starchlike polysaccharides.

2. The device of claim 1 wherein the kind and amount of cyclodextrin will enhance adsorption.

3. The device of claim 1 wherein said device has a variable geometry whereby after insertion in one geometry the device will assume another having a retention characteristic.

4. The device of claim 1 wherein said polymer is poly (ε-caprolactone).

5. The device of claim 1 wherein said polymer is a starch-like polysaccharide.

6. The device of claim 1 wherein the cyclodextrin is hydroxypropyl β-cyclodextrin.

7. The device of claim 1 wherein the cyclodextrin comprises from 5 to 70% w/w of the impregnated matrix.

8. The device of claim 1 wherein the progesterone comprises from 5 to 70% w/w of the impregnated matrix.

9. The device of claim 8 wherein the progesterone loading is from 0.1 to 3 gms.

10. The device of claim 8 wherein the surface area of the impregnated matrix is from 8 to 200 cm$^2$.

11. The device of claim 10 wherein said surface area is from 15 to 200 cm$^2$.

12. The device of claim 8 wherein progesterone does not appear as a fine powder or crystal upon the surface of the device.

13. An intra vaginal device for insertion into the vagina of an animal, said device being intra vaginally insertable, intra vaginally retainable and withdrawable by virtue of its ability to change geometry yet being formed at least almost exclusively from a cyclodextrin and progesterone impregnated moulding matrix of poly (ε-caprolactone), the loading of progesterone being from 0.1 to 3 gms and the surface area of the impregnated matrix being from 8 to 200 cm$^2$.

14. The device of claim 13 wherein the surface area is from 15 to 200 cm$^2$.

15. A method for animal group oestrus synchrony comprising the step of utilizing an intra vaginal device, said device being intra vaginally insertable, intra vaginally retainable and withdrawable by virtue of its ability to change geometry yet being formed at least almost exclusively from a cyclodextrin and progesterone impregnated moulding matrix of poly (ε-caprolactone), the loading of progesterone being from 0.1 to 3 gms and the surface area of the impregnated matrix being from 8 to 200 cm$^2$.

16. The method of claim 13 wherein said surface area is from 15 to 200 cm$^2$.

17. A method of manufacturing of an intra vaginal device an for insertion into the vagina of a target species mammal, said device being or having a moulded progesterone and cyclodextrin impregnated matrix of a biodegradable polymer selected from the group of poly esters and starch like polysaccharides, the cyclodextrin being of a kind and in such amount as will enhance release and/or adsorption which method comprises or includes the steps of including in the starting material(s) of said biodegradable polymer a distribution of both cyclodextrin and progesterone, and thereafter moulding the device or the impregnated matrix of the device therefrom.

18. The method of claim 17 wherein the whole device results from the moulding.

19. The method of claim 18 wherein the progesterone comprises from 5 to 70% w/w of the impregnated matrix.

20. The method of claim 17 wherein the cyclodextrin(s) comprise from 5 to 70% w/w of the impregnated matrix.

21. The method of claim 17 wherein said progesterone and cyclodextrin are pre-mixed prior to association with said polymerisable precursor.

22. A method of achieving in an animal (or in each animal of a group of animals) a blood serum level of progesterone of greater than 2 ng/ml for a period of at least 5 days, said method comprising inserting and retaining in the or each animal for at least the 5 day period an intra vaginal device being or having a moulded progesterone and cyclodextrin impregnated matrix of a biodegradable polymer selected from the group of poly esters and starch like polysaccharides, the cyclodextrin being of a kind and in such amount as will enhance release and/or adsorption.

23. The method of claim 22 when used for herd oestrus synchrony purposes and wherein there is an additional step of withdrawing each device to allow an onset of oestrus.

24. The method of claim 23 wherein said device has a loading of from 0.1 to 3 gms of progesterone.

25. The method of claim 24 wherein said device has an impregnated matrix surface of from 8 to 200 cm$^2$.

26. The method of claim 25 wherein the surface area is from 15 to 200 cm$^2$.

27. The method of claim 23 wherein the animal(s) is or are of the cattle, sheep, goats or deer species.

28. An intra vaginal device for insertion into the vagina of a target species mammal, said device being or having a moulded progesterone and cyclodextrin impregnated matrix of a biodegradable polymer selected from the group of poly esters and starch like polysaccharides, the cyclodextrin being of a kind and in such amount as will enhance release and/or adsorption, when made by a method which includes the steps including in the starting material(s) of said biodegradable polymer a distribution of both cyclodextrin and progesterone, and thereafter moulding the device of the impregnated matrix of the device therefrom.

* * * * *